(12) United States Patent
Bleuet et al.

(10) Patent No.: US 9,046,760 B2
(45) Date of Patent: Jun. 2, 2015

(54) IMAGING SYSTEM FOR IMAGING FAST-MOVING OBJECTS

(75) Inventors: Pierre Bleuet, Seyssins (FR); Denis Jalabert, Grenoble (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 393 days.

(21) Appl. No.: 13/555,341

(22) Filed: Jul. 23, 2012

(65) Prior Publication Data

US 2013/0028380 A1  Jan. 31, 2013

(30) Foreign Application Priority Data

Jul. 25, 2011 (FR) ...................................... 11 56773

(51) Int. Cl.
  *G03B 42/02* (2006.01)
  *G01N 23/04* (2006.01)
  *H04N 5/32* (2006.01)

(52) U.S. Cl.
  CPC ................ *G03B 42/02* (2013.01); *G01N 23/04* (2013.01); *H04N 5/32* (2013.01); *G01N 2223/314* (2013.01); *G01N 2223/41* (2013.01); *G01N 2223/611* (2013.01)

(58) Field of Classification Search
  CPC .................... G01N 2223/314; G01N 2223/41; G01N 2223/611; G01N 23/04; G03B 42/02; H04N 5/32
  USPC ................... 250/370.11, 361 R, 370.09, 362; 378/86, 87, 62, 43, 19
  See application file for complete search history.

(56) References Cited

U.S. PATENT DOCUMENTS

| 3,603,828 | A |   | 9/1971 | Sheldon |
| 4,220,975 | A | * | 9/1980 | Lieber et al. .................. 348/367 |
| 4,395,636 | A | * | 7/1983 | Anger et al. .................. 250/366 |

(Continued)

FOREIGN PATENT DOCUMENTS

| EP | 1 013 225 A1 | 6/2000 |
| GB | 2 377 275 A | 1/2003 |

(Continued)

OTHER PUBLICATIONS

Kotecki et al., "Optical shutters using microchannel plate (MCP) intensifier tubes", Proc. SPIE 0427, High Speed Photography, Videography, and Photonics I, 62 (Jan. 9, 1984).*

(Continued)

*Primary Examiner* — Michael Logie
(74) *Attorney, Agent, or Firm* — Oblon, McClelland, Maier & Neustadt, L.L.P.

(57) ABSTRACT

An imaging system intended for imaging fast-moving objects, comprising an X-ray source, a scintillating screen, a shutter and a detector of the beam emitted by the shutter, and a processing unit connected to the detector, where the shutter is positioned between the scintillator screen and the detector, and a support for the object to be observed is positioned downstream from the X-ray source and upstream from the scintillator screen, where the shutter is a shutter which can be controlled at high frequencies, for example higher than approximately 1 kHz, where the shutter is fixed and the transmission of the signal originating from the scintillator screen towards the detector is controlled by electrical polarization means controlled by a control unit.

23 Claims, 8 Drawing Sheets

(56) References Cited

U.S. PATENT DOCUMENTS

Figure 1A:
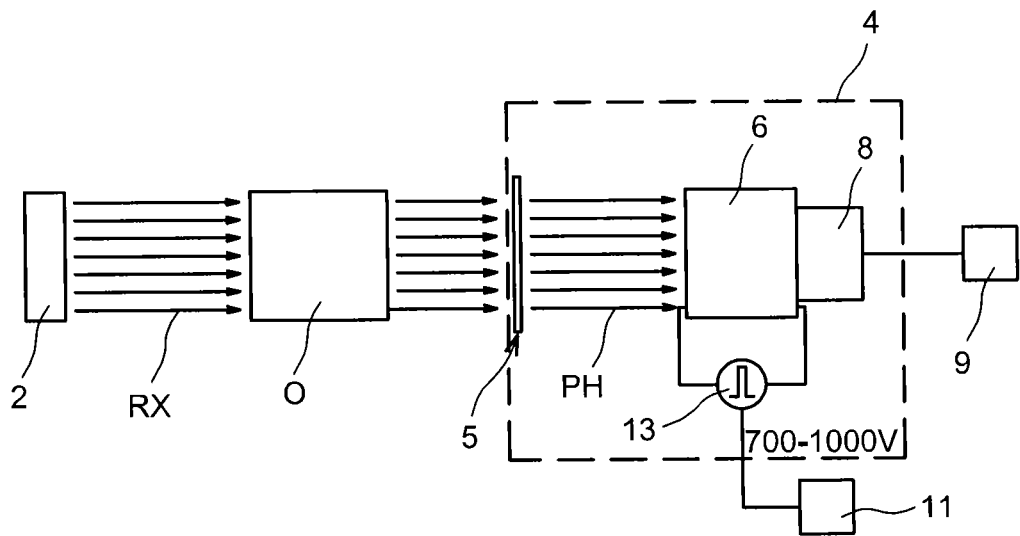

| | | | |
|---|---|---|---|
| 4,612,572 A * | 9/1986 | Komatsu et al. | 378/98.12 |
| 4,636,629 A | 1/1987 | Tosswill | |
| 4,671,102 A * | 6/1987 | Vinegar et al. | 73/61.48 |
| 4,996,413 A | 2/1991 | McDaniel et al. | |
| 5,878,107 A * | 3/1999 | Ishikawa et al. | 378/98.2 |
| 5,887,049 A | 3/1999 | Fossum | |
| 7,130,375 B1 * | 10/2006 | Yun et al. | 378/79 |
| 7,888,761 B2 | 2/2011 | Meyer et al. | |
| 8,433,037 B1 * | 4/2013 | Wood | 378/86 |
| 2001/0046276 A1 * | 11/2001 | Schneider et al. | 378/58 |
| 2005/0201518 A1 * | 9/2005 | De Groot | 378/98.8 |
| 2008/0075227 A1 | 3/2008 | Christoph et al. | |
| 2008/0205737 A1 | 8/2008 | Kunze et al. | |
| 2009/0272908 A1 | 11/2009 | Warner et al. | |
| 2010/0052118 A1 | 3/2010 | Galera et al. | |
| 2010/0208872 A1 * | 8/2010 | Karellas | 378/98.8 |
| 2011/0063617 A1 * | 3/2011 | Takahashi et al. | 356/370 |
| 2014/0072102 A1 | 3/2014 | Bleuet et al. | |

FOREIGN PATENT DOCUMENTS

| | | |
|---|---|---|
| JP | 63-26083 | 2/1988 |
| JP | 1-159615 | 6/1989 |
| JP | 5-153495 | 6/1993 |
| JP | 2010-181190 | 8/2010 |
| WO | WO 97/40620 | 10/1997 |

OTHER PUBLICATIONS

Preliminary Search Report issued Dec. 2, 2011 in French Application No. 1156773 (With English Translation of Category of Cited Documents).

Charles P. Beetz, et al., "Silicon-micromachined microchannel plates", Nuclear Instruments & Methods in Physics Research, A, vol. 442, 2000, pp. 443-451.

Wen H. Ko, et al., "Trends and frontiers of MEMS", Sensors and Actuators, A, vol. 136, 2007, pp. 62-67.

A. C. Kak, et al., "Principles of Computerized Tomographic Imaging", Chapter 3 and 7, IEEE Press, 1988, 86 pages.

Marco Cammarata, et al., "Chopper system for time resolved experiments with synchrotron radiation", Review of Scientific Instruments, vol. 80, 2009, pp. 015101-1 to 015101-10.

European Search Report issued Oct. 10, 2012, in European Patent Application No. 12177430.

* cited by examiner

FIG.4A
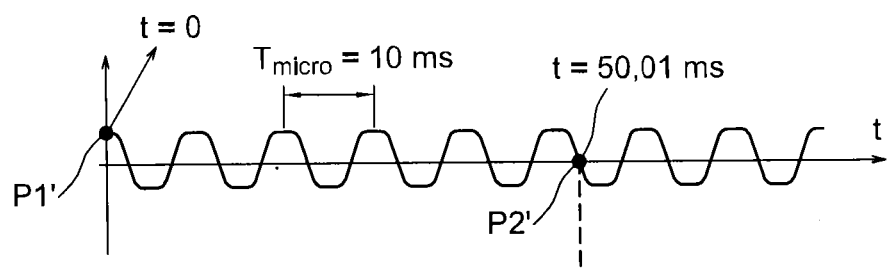
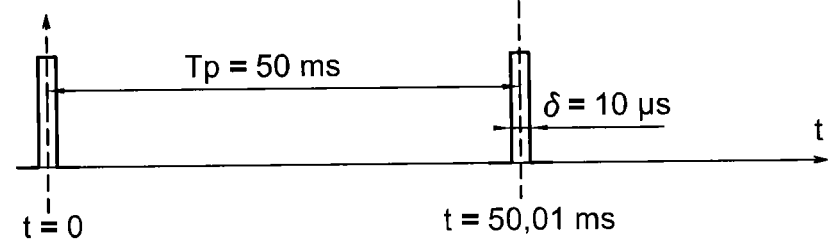
FIG. 4B

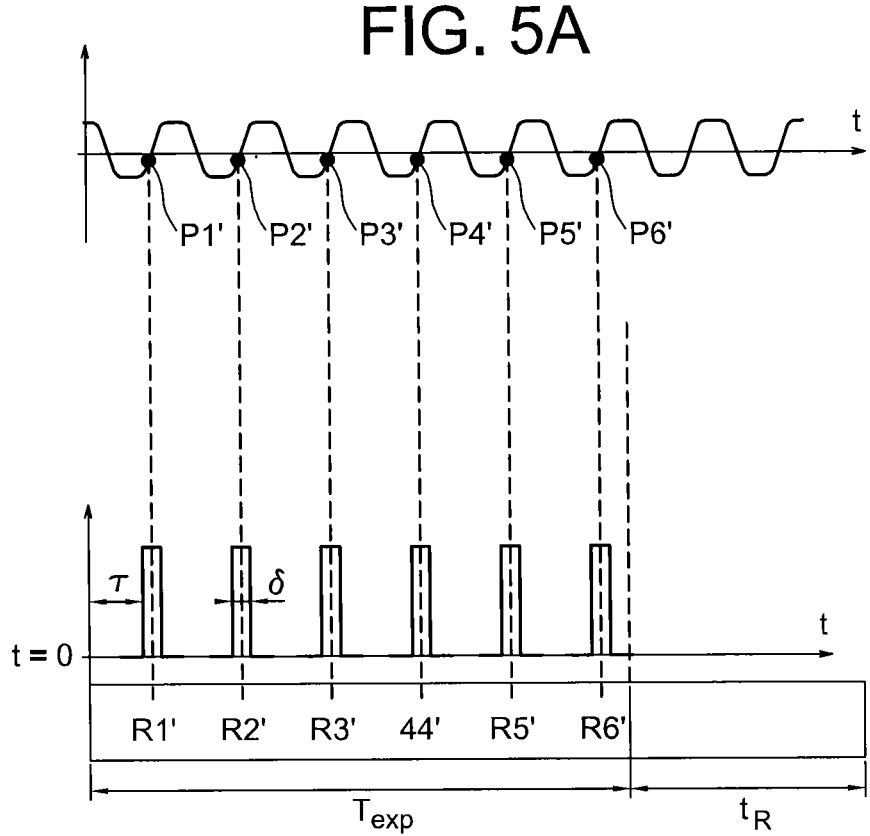

IMAGING SYSTEM FOR IMAGING FAST-MOVING OBJECTS

TECHNICAL FIELD AND PRIOR ART

The present invention relates to an imaging system for imaging fast-moving objects, particularly MEMS (microelectromechanical systems) systems and NEMS (nanoelectremechanical systems) systems.

Amongst MEMS and NEMS there are oscillators with periodic movement; this concerns, for example, RF switches or certain gyroscopes. These MEMS and NEMS are objects known as "buried" objects, i.e. they are enclosed in silicon. Observation by means of electron microscopy, optical microscopy, electrical characterisation or laser vibrometry is ineffective: the silicon protection is opaque to electrons and to light photons, and the electrical characterisation provides no images.

For purposes of simplicity, both MEMS and NEMS will be designated below by the term "microsystems".

The aim is to analyse their properties when their moving portions oscillate, to understand their operation and the reasons for which they can be subject to a malfunction.

For example, when uncovering microsystems which were no longer operating, a transfer of matter between the fixed portion and the moving portion has been observed.

However, the process of this transfer of matter has not been able to be observed. In the case of RF switches, the presence of nanowires causing a short circuit has been observed, but the phenomenon of the appearance of these nanowires also remains unobserved.

Consequently, observation of the microsystems whilst in movement would be useful in order to be able to optimise their structures.

In order to observe buried objects X-ray imaging can be used. For example, imaging systems by X-rays exist, comprising an X-ray source, a shutter upstream from the object to be observed, and means of detection of the rays transmitted by the object. The shutter is a mechanical shutter which is made of lead in order to stop the X-rays completely outside the exposure period, however. The shutter is moved to interrupt or allow illumination of the object. Due to the inertia of the shutter, and for mechanical and stability reasons, such shutters cannot be used for microsystem operating frequencies which are between approximately 1 kHz and approximately 1 GHz.

DESCRIPTION OF THE INVENTION

Consequently, it is one aim of the present invention to provide an imaging system allowing fast-moving buried microsystems to be imaged.

The aim of the present invention is achieved by means of a system comprising an X-ray source, a scintillator screen to convert the X-rays into visible radiation, a fixed detector and a fixed shutter, positioned between the scintillator screen and the detector, where the shutter is able to change from an on-state to an off-state at a frequency of greater than 1 kHz, and a unit to control the shutter.

The shutter can be formed by a microchannel plate which, in addition to a very high switching frequency, also has the advantage that it amplifies the signal transmitted by the microsystem. Exposure times of between 10 ns and 100 ns can be attained.

As a variant, the shutter can be formed by a polarised liquid crystal mirror. Exposure times of 1 ms can be attained.

This system allows stroboscopic detection in the case of microsystems involving periodic movements.

The system also enables a radiogram of the microsystem to be obtained at a given moment by synchronising the movement of the microsystem and the state of the shutter.

By means of the system according to the present invention it is also possible to obtain a 4-D observation (3 spatial dimensions and 1 temporal dimension) of the microsystem by implementing a system of observation by tomography.

The subject-matter of the present invention is then an imaging system intended for imaging fast-moving objects, comprising an X-ray source, a scintillator screen, a shutter and a detector of the beam emitted by the shutter and a processing unit connected to the detector, where the shutter is positioned between the scintillator screen and the detector, and a support for the object to be observed is positioned downstream from the X-ray source and upstream from the scintillator screen, where the shutter is a shutter which can be controlled at high frequencies, for example frequencies higher than approximately 1 kHz, where the shutter is fixed and where the transmission of the signal originating from the scintillator screen towards the detector is controlled by electrical polarisation means controlled by a control unit, where said imaging system also comprises means for actuating the said object such that they cause the moving portion to move relative to the fixed portion.

In an example embodiment the shutter comprises at least one microchannel plate. As a variant the shutter is formed by two microchannel plates positioned one behind the other.

A residual polarisation can be applied to one of the faces of a plate.

The control unit advantageously controls the polarisation means such that they send voltage pulses at a frequency of between 1 Hz and 20 MHz. The duration of a pulse is, for example, of between 10 ns and 100 ns.

In another example embodiment the shutter comprises at least one liquid crystal mirror aligned relative to the scintillator screen and relative to the detector, such that it reflects the beam originating from the scintillator screen towards the detector when it is polarised. The control unit can control the polarisation means such that they send the liquid crystal mirror voltage pulses at a frequency of less than 1 kHz. For example, the duration of a pulse is of the order of 1 ms.

Advantageously, the support is able to pivot through a given angular pitch around an axis perpendicular to the axis of emission of the X-ray source. The angular pitch may be variable.

According to an additional characteristic, the control unit can control the movement of the microsystem. The control unit can comprise means to shape signals to control the object with a programmable delay, where the said shaped signals are used to control the polarisation means.

The detector can, for example, be a charge-coupled device. As a variant the detector is a CMOS sensor.

Another subject-matter of the present invention is an imaging method using an imaging system according to the present invention, in which the object moves periodically and the system is used to accomplish stroboscopic detection, so as to obtain images at several states of the object.

Another subject-matter of the present invention is an imaging method using an imaging system according to the present invention, in which the control unit controls the polarisation means according to the signal controlling the movement of the object.

The control unit can form a signal for controlling the polarisation means from the signal for controlling the object by introducing a programmable delay; the duration of the delay is modified so as to image several states of the object.

The object can be pivoted around an axis perpendicular to the axis of the X-ray emission axis, so as to produce images of the object in different angular positions. The angular pitch may be variable.

The imaging method may comprise
the step of mathematical reconstruction of the three-dimensional images of the object at each angular position.
the step of concatenation of the three-dimensional images.

For example, the object imaged by the imaging process is a microelectromechanical system or a nanoelectromechanical system.

BRIEF DESCRIPTION OF THE ILLUSTRATIONS

Figure 1B:
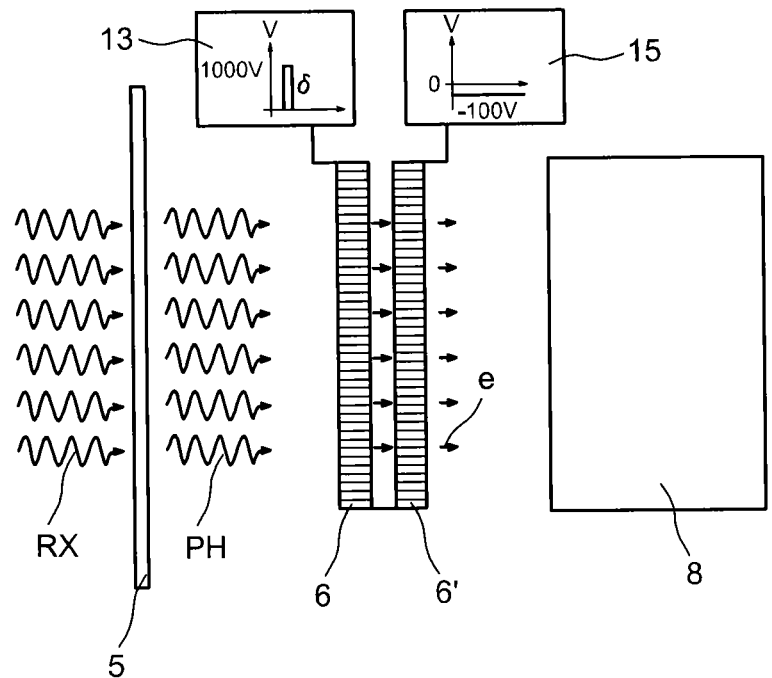
Figure 2:
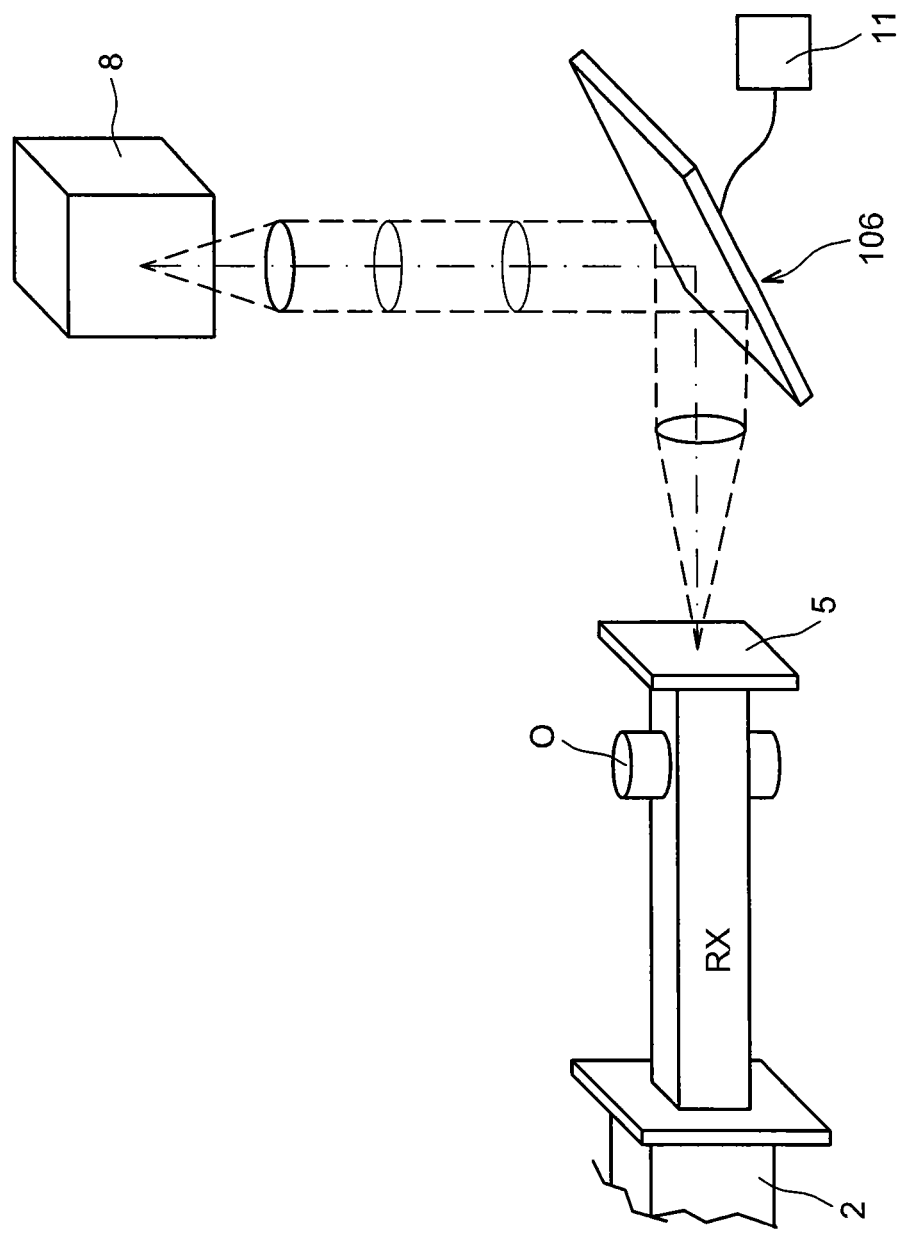
Figures 3A, 3B:
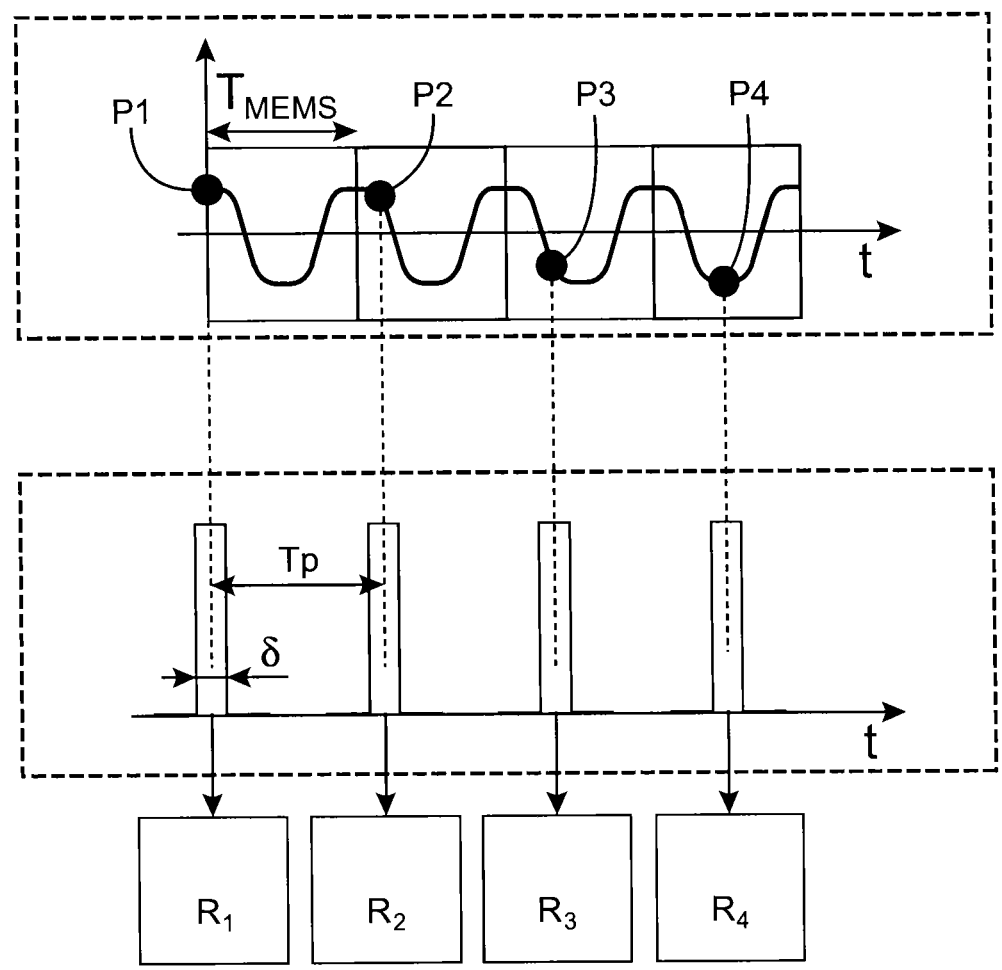
Figure 6:
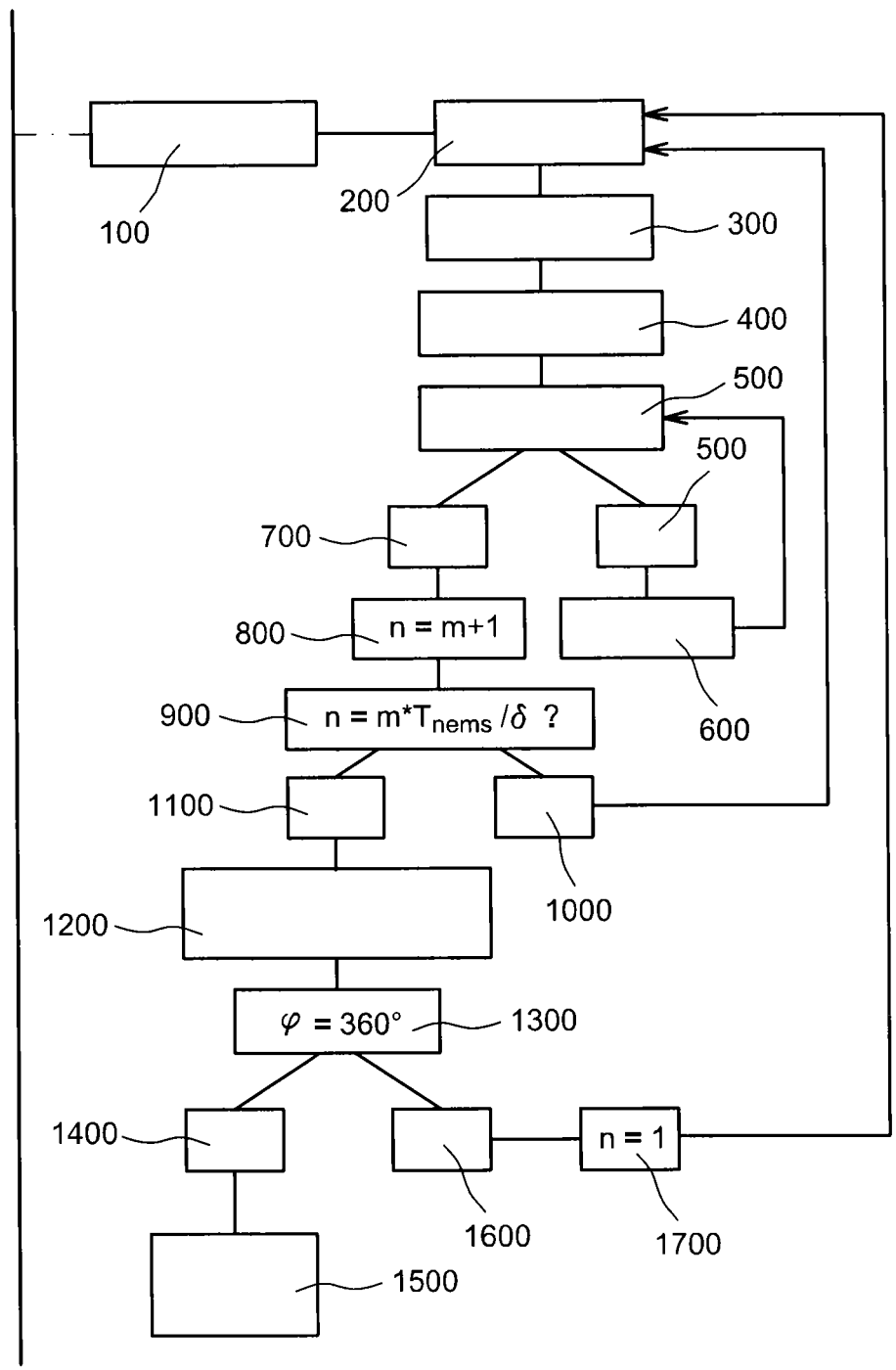
Figure 7:
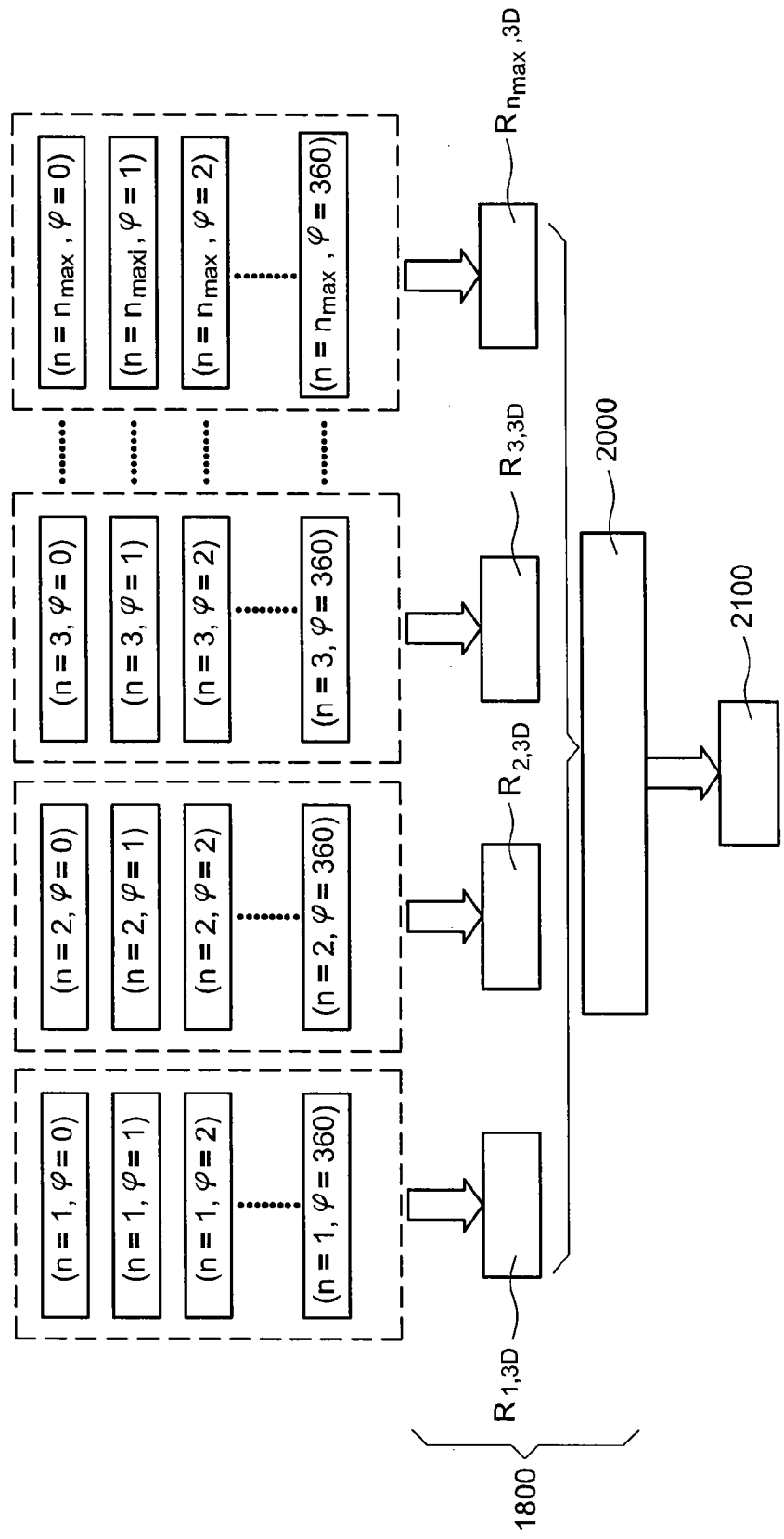
Figure 8:
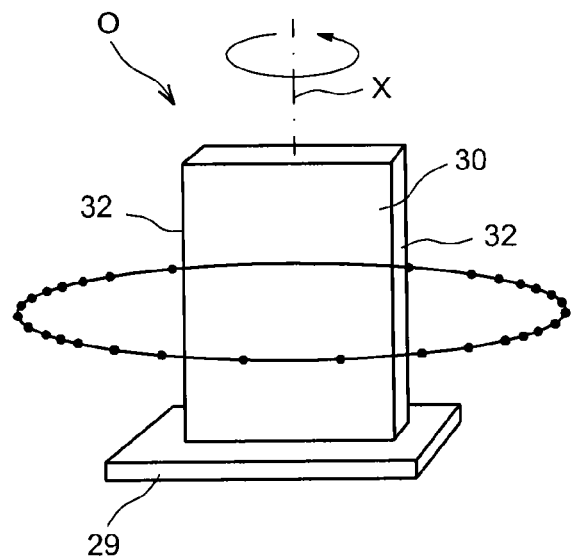
Figure 9:
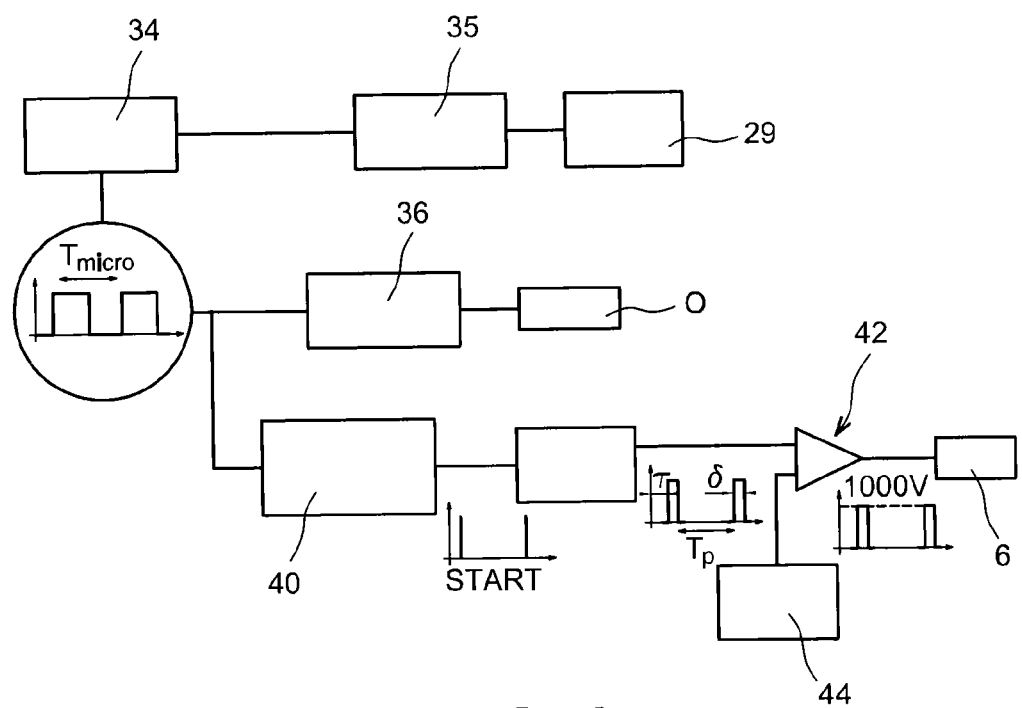

The present invention will be better understood using the description which follows and the appended illustrations, in which:

FIG. 1A is a schematic representation of an example embodiment of an imaging system according to the invention, where the shutter is formed by a microchannel plate, FIG. 1B is a representation of a variant of the system of FIG. 1, in which the shutter comprises two microchannel plates, FIG. 2 is a schematic representation of another example embodiment of an imaging system according to the invention, where the shutter is formed by a liquid crystal mirror, FIGS. 3A and 3B are graphical representations, respectively of the periodic movement of a microsystem and of the control of the shutter over time, in order to accomplish stroboscopic detection, FIGS. 4A and 4B are graphical representations, respectively of the periodic movement of a microsystem and of another control of the shutter over time, in order to accomplish stroboscopic detection, FIGS. 5A and 5B are graphical representations respectively of a microsystem excitation signal imposed by the control unit and of the shutter control signal over time, where the control of the shutter is synchronised with the movement of the microsystem, FIG. 6 is a flow chart of the steps of a method of operation of the imaging system according to the invention allowing 4-D imaging to be accomplished, FIG. 7 represents schematically the recording steps accomplished following the implementation of the steps of the flow chart of FIG. 6, FIG. 8 is a schematic representation of the rotation imparted to the object to be observed if the latter has a large aspect ratio, FIG. 9 is a schematic representation of the measuring sequence to produce the 4-D imaging with the system according to the invention.

DETAILED ACCOUNT OF PARTICULAR EMBODIMENTS

In FIG. 1A a schematic representation of an imaging system according to the present invention can be seen comprising an X-ray source 2 intended to be positioned upstream from object O which is to be illuminated, an assembly 4, designated RC in the figures, for collecting the X-rays transmitted by object O.

In the following description the images obtained by the system according to the invention will be designated a "radiogram", and in the illustrations will be designated by "R".

Assembly 4 comprises a scintillator screen 5 converting the X-rays into visible light, a shutter 6 and a lens 8 for collecting and recording digitally the visible light transmitted by the object and the shutter and a fast electronic processing unit or control unit 11 for controlling shutter 6. Control unit 11 also controls actuation of the microsystem. The actuation of the microsystem can be thermal, electrostatic or magnetic.

Very advantageously, the microsystems are powered in wireless fashion and without contact by an external power source, which enables the uncontrolled movements of the microsystems due to rotating wires, which occurs in tomographic mode, to be eliminated.

The microsystem is powered, for example, by RF waves. Such actuation means to actuate an MEMS stress sensor are described, for example, in document Wen H. Ko, "*Trends and Frontier of MEMS*", in Sensors and Actuators A 136 (2007) 62-67; the signals emitted by the sensor are also read advantageously in wireless fashion.

The optical detection device is formed, for example, by a sensor of the charge-coupled device type, or CCD sensor: fitted with a scintillator which converts the electrons into visible radiation. As a variant, a direct-conversion electron detector could be used. These sensors are well known to the skilled man of the art and are, for example, described in document U.S. Pat. No. 7,888,761.

As another variant, CMOS sensors which have a shorter read time than CCD sensors could be used; however they have a less satisfactory dynamic range. The detection lens is connected to a processing unit 9 to which the images are sent.

In the represented example, and advantageously, shutter 6 is formed by a microchannel plate (MCP). An MCP is a silicon plate pierced by a large number of microchannels, which are typically 10 µm in size. This plate is subjected to a voltage of several hundred volts, such that every incident particle in a microchannel which strikes the wall creates a spray of electrons which are themselves accelerated and channelled along the microchannel. An MCP thus enables charges to be amplified. The article Charles P. Beetz, Robert Boerstler, John Steinbeck, Bryan Lemieux, David R. Winn "*Silicon-micromachined microchannel plates*"; Nuclear Instruments and Methods in Physics Research A 442 (2000) 443} 451 describes such plates. Use of one or more microchannel plates is particularly suited to the observation of microsystems, since the diameter of the channels is of the order of 10 µm, a dimension which is consistent with the observation resolution of MEMS and NEMS systems.

When the plate is polarised it converts the visible photons (represented by arrows and designated PH) and UV photons deriving from the scintillator screen into electrons (represented by arrows and designated e in FIG. 1B), and amplifies the electronic current sent to the CCD sensor. If there is no polarisation the plate is opaque to this same radiation.

The imaging system comprises a voltage generator 13 to polarise the shutter. The voltage pulses are of the order of 700 V to 1000 V.

For example, the control unit polarises plate 6 using a voltage of between 700 V and 1100 V for very short time intervals δ of the order of 10 ns to 100 ns, where δ is the exposure time, controlling the image acquisition time.

A residual polarisation of the order of 100V can be applied to one of the faces of the plate to eliminate the charges created by the optical radiation in the plate during the shuttering phases.

This image acquisition can occur at a very slow rate, for example at a frequency of the order of 1 Hz, up to fast frequencies of the order of 2-20 MHz, corresponding to f~½δ. In addition to its operation over a very broad frequency range, microchannel plates have the advantage that they amplify the electronic current sent to the sensor.

As will be seen below, this acquisition frequency is not necessarily regular, and can be controlled by an external generator. In particular, the frequency which controls oscillation of the microsystem can be chosen as the control, by applying an adjustable delay to it.

In FIG. 1B a variant of the system of FIG. 1A can be seen, in which the shutter is formed from two microchannel plates in series, where each amplifies the input signal, enabling the gain to be improved. The upstream plate is polarised by pulse generator 13, and a residual polarisation is applied to the downstream plate by means 15. Both plates in combination form a single shutter.

In FIG. 2 another example of an imaging system can be seen in which shutter 106 is formed by a polarised liquid crystal mirror. Depending on the polarisation, the visible image sent by the scintillator screen may or may not be reflected by the mirror towards the CCD sensor. The minimum exposure time can be of the order of 1 ms. In this case the CCD receives photons directly, rather than electrons. In the case of a mirror this is a CCD sensor of the conventional type, with a photoactive region which converts the visible photons into electrons, following which the created charges are read and the image is formed in this manner. This sensor is well known to the skilled man of the art and is, for example, described in document U.S. Pat. No. 4,996,413.

This imaging system is therefore particularly advantageous in the case of slow-moving microsystems.

We shall now describe the implementation of the imaging system according to the invention to accomplish stroboscopic detection. This detection applies to microsystems having periodic movement.

The read times of CCD sensors are very long. Stroboscopy is thus used to image dynamically changes of microsystems having periodic movement. To this end, the voltage of the shutter is controlled such that a radiogram is acquired at different states of the microsystem. The time between two pulses is at least equal to the CCD sensor's read and record time.

In FIG. 3A the position of a microsystem which it is desired to observe over time is represented graphically. Points P1 to P4 are the instants of the movement during a period which it is desired to observe. R1 to R4 are radiograms taken at these instants P1 to P4.

In FIG. 3B the voltage pulses of the shutter sent by the electronic processing unit are represented. Each pulse corresponds to an instant P1 to P4 of the movement, and the duration of the pulse represents the images' time resolution.

Reading and recording of the sensor take place between two pulses.

Since the movement is periodic it is possible, by recording images over several periods, to obtain a film of the microsystem's periodic movement.

FIGS. 4A and 4B represent the process of sequential recording of the radiograms in stroboscopy mode under the following conditions:

Exposure time of the microsystem to X-rays: $\delta=10\,\mu s$. This period determines the time resolution and is equal to the duration of the pulse applied to the shutter.

Period of movement of the microsystem: Tmicro=10 ms, Read and record time of the CCD sensor: $t_{read}=50$ ms. Period $T_p$ of the pulses applied to the shutter is:

$T_p \geq T_{micro}+\delta$, i.e. $T_p \geq 50.01$ s.

Two radiograms of the microsystem are therefore obtained, one at t=0 s and the other at t=50 ms+10 μs=50.01 ms. If the movement of the microsystem is periodic with a period of 10 ms, the radiogram at t=50.01 ms is equivalent to a radiogram at 0.01 ms=10 μs.

In this particular example, the acquisition method therefore enables the movement of the microsystem to be sampled every 10 μs.

We shall now describe a method of detection of the movement of a microsystem, where the latter may or may not have a periodic movement.

In FIG. 5A a graph representing the excitation signal applied to the microsystem over time can be seen. Points P1' to P6' represent the instants which it is desired to observe. R1' to R6' are radiograms taken at these instants P1' to P6'.

This method connects the excitation signal of the microsystem and the shutter. To this end the signal which controls the microsystem is used to control the shutter. The control unit transmits the signal controlling the microsystem, and shapes this signal by introducing a programmable delay τ which enables the instant to be determined, and therefore the state of the microsystem which it is desired to observe. Duration δ over which the shutter illuminates the CCD sensor is determined. The signal transformed in this manner is sent to the voltage generator.

In FIG. 5B the signal controlling the shutter can be seen represented, in the form of voltage pulses, formed from the microsystem's control signal, together with the delay τ between the start of the system's excitation signal and point P1' to be detected, and the CCD sensor's illumination duration δ.

This configuration enables a radiogram of the microsystem at a determined state to be acquired.

The choice of time lag τ applied between the movement of the microsystem and the acquisition of the radiogram enables the object to be observed in different states whilst it moves.

In order to observe different states of the microsystem, delay τ is modified.

The period between 2 pulses can then be much shorter than read and record time $t_R$ of the CCD sensor. The choice of the shutter's voltage application time δ enables the images' time resolution to be adjusted.

In FIG. 5A the repetition of the illumination at instants P2' to P6' is represented such that instants P2' to P6', during which the microsystem is in the same state as at instant P1', are observed. This therefore amounts to taking six images of the microsystem in the same state. The CCD sensor is then exposed for a total duration corresponding to the number of pulses of the shutter over exposure time $T_{exp}$ of the CCD sensor, i.e. 6×δ in the example of FIG. 4B. The 6 images are totalled, which therefore enables the quality of the images to be improved by improving the signal-to-noise ratio. This method applies to periodic or repeatable movements; a method is said to be repeatable when it is reproduced identically, but not necessarily periodically. For example, in the represented case, it may be considered that the movement is repeated eight times in succession, and identically.

By means of the invention it is therefore possible to obtain images R1' to R6' in two dimensions of all the states of the microsystem; a film of the movement of the buried microsystem can therefore be obtained. It is therefore possible to observe the changes of the state of the microsystem in the course of its operation, and observe, for example, causes of damage and/or the mass transfer phenomenon.

We shall now describe a system and a method enabling reconstruction in 4 dimensions (3 spatial dimensions and the temporal dimension). To this end, the system is associated with a technique of detection by tomography; the system then comprises a support for the object to be observed which rotates around an axis and can move the object through a given angle so as to modify the viewpoint of the microsystem's CCD sensor.

The images obtained at each angle of view are produced by stroboscopic detection or by synchronisation between the movement of the microsystem and the control of the shutter.

The support is controlled by a central unit which causes the support to pivot when all the images of a viewpoint have been taken.

In FIG. 6 a flow chart of the method of 4-D reconstruction according to the present invention is represented.

The microsystem is positioned on the support; initial angle of rotation φ is equal to 0.

n is the number of images in each period of the microsystem, the initial value of which is 1.

$T_{micro}$ is the period of the microsystem.

δ is the exposure time.

t is the time.

By setting δ the sampling of the microsystem's movement is determined. If sampling is set to δ, it is desired to make $T_{micro}/\delta$ images in each period, or a multiple of this number.

Firstly, during a step 100; the microsystem is actuated.

After this, in a step 200, a voltage pulse is sent to the shutter during a period δ.

During a step 300 the CCD sensor reads and records the image.

At the end of this step a check is made in step 400 as to whether t is congruent with nδ modulo $T_{micro}$, which is written t=nδ[$T_{micro}$].

If the response is No (step 500), the system waits until the condition of step 400 is checked (step 600).

If the response is Yes (step 700), n is incremented by 1 (step 800).

In step 900, a check is made as to whether n, i.e. the number of images actually made, is a multiple of the number of images which it is desired to acquire in each period, i.e. when the sampling has been chosen, a check is therefore made as to whether n=m×$T_{micro}/\delta$, where m is a positive integer.

If the response is No (step 1000), we return to step 200 to make a new image.

If the response is Yes (step 1100), in step 1200 the object is pivoted by rotating the support through a given angle. This may be a constant angle equal to 360°/$N_\phi$, where $N_\phi$ is the predetermined number of viewpoints. φ may vary according to the shape of the object, as we shall see below.

In step 1300 a check is made as to whether the angle by which the object has been pivoted is equal to 360°. If the response is Yes (step 1400), this means that the object has gone through a complete revolution, and that all the shots have been taken. This then leads to step 1500, which is the end of the analysis.

If the response is No (step 1600), n is reset to the value 1 (step 1700) and the analysis method continues at step 200.

In FIG. 7 a recording sequence of the images resulting from the method of FIG. 6 and the 4-D reconstruction can be seen in a schematised manner. The recording sequence is made in lines $n_{max}$ is the number of images actually taken for each viewpoint or angle of rotation of the microsystem; $n_{max}$ is a multiple of $T_{micro}/\delta$.

After $n_{max}$ images taken for each angle of rotation, a mathematical reconstruction of each state of the microsystem is made at the different angles of rotation (step 1800). On the basis of the representation of FIG. 7 the mathematical reconstruction is made for each column. A representation in 3 dimensions of each state of the microsystem is then obtained, where each state is separated by δ. These representations are designated $R_{1, 3D}, R_{2, 3D}, R_{2, 3D}, \ldots R_{nmax3D}$.

This mathematical reconstruction is made by techniques known to the skilled man in the art; it may use the Filtered Backprojection method, the Algebraic Reconstruction Technique method, and all their variations described, for example, in A. C. Kak, M. Slaney, *Principles of Computerized Tomographic Imaging*, IEEE Press, 1988. The latter will not be described in detail.

A concatenation of the 3-D volumes is then accomplished (step 2000) in order to obtain a 4-D representation of the buried microsystem (step 2100).

In FIG. 8, a representation of an object with a diagrammatic representation of the variable angular pitch of the different viewpoints during the acquisition can be seen, i.e. an irregular angular sampling.

This is particularly advantageous in the case of objects with large aspect ratios, which is generally the case with microsystems. It is then preferable during the rotation movement to take images with a very fine angular pitch at certain alignments, whereas in the case of other alignments the angular pitch may advantageously be chosen to be larger in order to reduce the analysis time.

In the represented example, object O is parallelepipedic in shape, its lengthways axis X being aligned with the axis of rotation of support 29. The object's thickness is very small compared to its length and its width. It has two large-size lateral faces 30, which are parallel to the lengthways axis, and two small-size lateral faces 32. The angular pitches are represented diagrammatically by points. In order to reduce the analysis time it is then advantageous to have a fine angular pitch during the observation of the zones of transition between faces 30 and a face 32 in order to have a large number of shots (high point density), since the observed configuration changes substantially over a small angular distance, and a larger angular pitch when the analysis concerns faces 30, since over a large angular distance the observed configuration changes only slightly (lower point density).

In FIG. 9 the control and processing portion of the system to accomplish a 4-D reconstruction is represented, in which the polarisation of the shutter is synchronised with the movement of the microsystem, comprising a computer 34 forming a control unit and processing unit, which controls the positioning of the object by controlling a rotation controller 35 controlling the rotation of support 29, controls a signal generator 36 which controls the microsystem controls the shutter. A discriminator 40 generates a pulse designated START in FIG. 9 on the rise (or fall) front of the signal controlling the microsystem. This START pulse is shaped with a delay T and a programmable width δ. The signal shaped in this manner is amplified by an amplifier 42 to a high voltage 44, which is also programmable, applied directly to the shutter. In the case of a microchannel plate this high voltage is adjusted so as to control the gain of the microchannel plate.

The CCD sensor sends the images collected during the plate's opening time to the computer, which then accomplishes the 4-D reconstruction.

Advantageously, it may be decided, in order to accelerate the analysis further, to use only a limited number of radiograms, less than the theoretical number, and to compensate for this smaller number by using ART (algebraic reconstruction technique) iterative algorithms. For example, some hundred projections will be used for a detector with 2000×2000 pixels, instead of the 3000 theoretically necessary projections. Such a method is described, for example, in patent US 2008/0205737.

The invention claimed is:
1. A system for imaging an object, the object being configured to perform a movement in response to an incoming signal, and where the system comprises:
   an X-ray source;
   a scintillator screen;
   a fixed shutter configured to be controlled at high frequencies;
   a detector of the beam emitted by the shutter, the shutter being positioned between the scintillator screen and the detector;
   a processor connected to the detector;
   a support for the object to be observed positioned downstream from the X-ray source and upstream from the scintillator screen; and
   a controller configured to control a voltage generator to polarize the shutter to allow transmission of the signal originating from the scintillator screen towards the detector, the controller being further configured to control transmission of a wireless signal to cause the object to perform the movement, wherein the controller is configured to control the voltage generator to polarize the shutter according to a timing of the transmission of the wireless signal.
2. An imaging system according to claim 1 in which, in the case of objects with periodic movements, the controller controls the voltage generator according to the frequency of the said movements.
3. An imaging system according to claim 1, in which the wireless signal transmission is thermal, electrostatic or magnetic transmission.
4. An imaging system according to claim 1, in which the shutter comprises at least one microchannel plate.
5. An imaging system according to claim 4, in which the shutter is formed by two microchannel plates positioned one behind the other.
6. An imaging system according to claim 4, in which a residual polarisation is applied to one of the faces of a plate.
7. An imaging system according to claim 4, in which the controller controls the voltage generator to send voltage pulses at a frequency of between 1 Hz and 20 MHz.
8. An imaging system according to claim 7, in which the duration of a pulse is between 10 ns and 100 ns.
9. An imaging system according to claim 1, in which the shutter comprises at least one liquid crystal mirror aligned relative to the scintillator screen and relative to the detector, such that it reflects the beam originating from the scintillator screen towards the detector when it is polarised.
10. An imaging system according to claim 9, in which the controller controls the voltage generator to send the liquid crystal mirror voltage pulses at a frequency of less than 1 kHz.
11. An imaging system according to claim 10, in which the duration of a pulse is of the order of 1 ms.
12. An imaging system according to claim 1, in which the support is able to pivot through a given angular pitch around an axis perpendicular to the axis of emission of the X-ray source.
13. An imaging system according to claim 12, in which the angular pitch is variable.
14. An imaging system according to claim 1, in which the controller is configured to shape the signals for controlling the movement of the object with a programmable delay, where said shaped signals are used for controlling the voltage generator.
15. An imaging system according to claim 1, in which the detector is a charge-coupled device or a CMOS sensor.
16. An imaging system according to claim 1, wherein the shutter is controlled at high frequencies higher than approximately 1 kHz.
17. An imaging system according to claim 1, in which the object has a periodic movement and the system is used to accomplish a stroboscopic detection, so as to obtain images at several states of the object.
18. An imaging system according to claim 17, in which the object is pivoted around an axis perpendicular to the X-ray emission axis so as to produce images of the object in different angular positions.
19. An imaging system according to claim 18, in which the angular pitch is variable.
20. An imaging system according to claim 18,
   the system being configured to perform mathematical reconstruction of the three-dimensional images of the object at each angular position and concatenation of the three-dimensional images.
21. An imaging system according to claim 17, in which the object is a microelectromechanical system or a nanoelectromechanical system.
22. An imaging system according to claim 1, in which the controller controls transmission of the signal for controlling the movement of the object by introducing a programmable delay; the duration of the delay is modified so as to image several states of the object.
23. A method implemented on a system for imaging an object, the object being configured to perform a movement in response to an incoming signal, and the system including an X-ray source, a scintillator screen, a fixed shutter configured to be controlled at high frequencies, a detector of the beam emitted by the shutter, the shutter being positioned between the scintillator screen and the detector, a processor connected to the detector, and a support for the object to be observed positioned downstream from the X-ray source and upstream from the scintillator screen, the method comprising:
   controlling, by a controller, a voltage generator to polarize the shutter to allow transmission of the signal originating from the scintillator screen towards the detector; and
   transmitting a wireless signal to cause the object to perform the movement,
   wherein the controlling of the voltage generator to polarize the shutter is made according to a timing of the transmission of the wireless signal.

* * * * *